Figure 1:
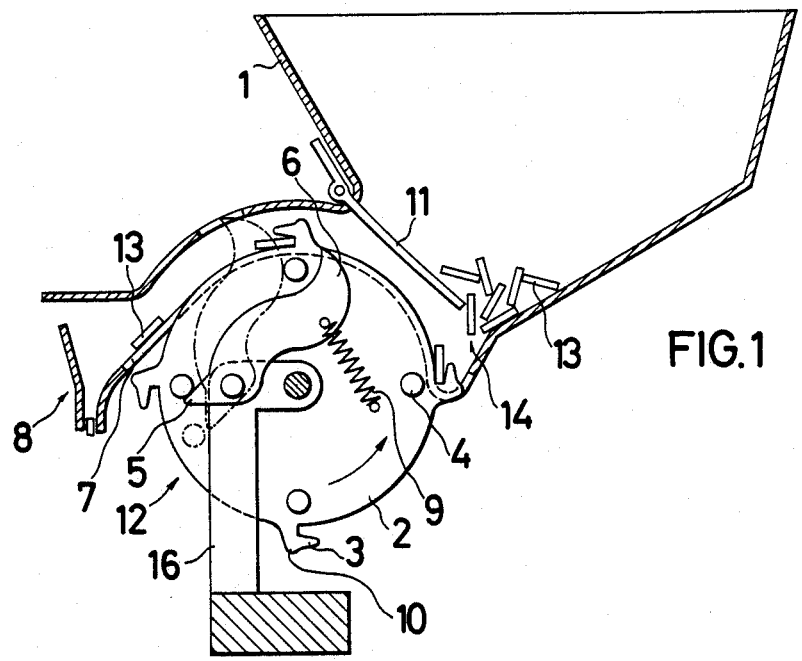

United States Patent [19]

Sänger

[11] Patent Number: 4,796,744
[45] Date of Patent: Jan. 10, 1989

[54] APPARATUS FOR SEPARATING TEST STRIPS

[75] Inventor: Hans D. Sänger, Frankfurt am Main, Fed. Rep. of Germany

[73] Assignee: Hoechst Aktiengesellschaft, Frankfurt am Main, Fed. Rep. of Germany

[21] Appl. No.: 78,661

[22] Filed: Jul. 28, 1987

[30] Foreign Application Priority Data

Jul. 30, 1986 [DE] Fed. Rep. of Germany ....... 3625697

[51] Int. Cl.$^4$ .............................................. B65G 47/24
[52] U.S. Cl. ................................... 198/397; 198/483.1
[58] Field of Search ................... 198/397, 443, 483.1, 198/526, 533, 478.1, 481.1, 634, 635; 221/167, 168

[56] References Cited

U.S. PATENT DOCUMENTS

| 1,353,356 | 9/1920 | Lee ........................................ 198/443 |
| 1,613,122 | 1/1927 | Ouellette ............................. 198/533 |
| 2,581,720 | 1/1952 | Schulte ................................ 198/533 |
| 2,858,862 | 11/1958 | Francisco ........................ 198/483.1 |

Primary Examiner—Joseph E. Valenza
Attorney, Agent, or Firm—Finnegan, Henderson, Farabow, Garrett, & Dunner

[57] ABSTRACT

In the apparatus for separating test strips, a supply container (1) for the test strips (13) is provided with an orifice (14). Arranged in this orifice (14) is a transport device (12) which is equipped with a guide plate (7) and with drivers (3) and which has noses (10, 19). The noses (10, 19) interact with a movably arranged bar (11) which projects into the orifice of the container.

1 Claim, 1 Drawing Sheet

U.S. Patent      Jan. 10, 1989      4,796,744

APPARATUS FOR SEPARATING TEST STRIPS

The invention relates to an apparatus for separating test strips having at least one test zone, such as are used, for example, for medical tests, especially for analyzing urine. It is part of a line serving for the automatic feeding, sorting and insertion of test strips in an analyzer, for example a multi-channel photometer.

For generally known urine diagnostics, multiple urine test strips for determining bilirubin, urobilinogen, ketone bodies, ascorbic acid, glucose, protein, nitrite, pH and blood are available for example. Test strips of this type contain several test zones, on which the reagents belonging to the particular test are arranged as indicators. The test strips are moistened with urine by hand and are subsequently introduced into the analyzer. This work is to be automated. Among other things, an apparatus for separating the test strips is necessary for this purpose.

The invention achieves the part object by a supply container for the test strips being provided with an orifice, in which is arranged a transport device equipped with a guide plate and with drivers and having noses which interact with a moveably arranged bar projecting into the orifice of the container.

The transport device can comprise a roller with drivers on its outer surface, and the drivers can be designed as noses. On at least one of the end faces of the roller there can be bolts which interact with a pawl connected to a return device. However, the transport device can also comprise a conveyor belt which is guided via deflecting rollers and which is equipped with drivers. The deflecting roller located opposite the orifice in the container can have the noses which interact with the moveably arranged bar projecting into the orifice. The bar is appropriately moved by the noses in such a way that the test strips slip into the orifice and bridge formation is prevented.

The invention is explained in detail below with reference to drawings illustrating only one possible embodiment. In the drawings:

FIG. 1 shows a sectional side view of the apparatus, and

Figure 2:
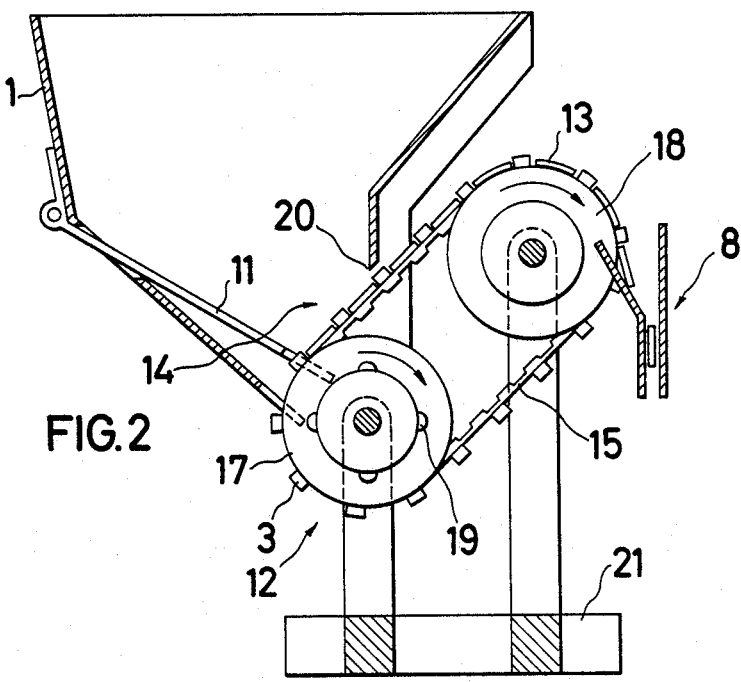

FIG. 2 likewise shows a sectional side view of an alternative form of the apparatus according to FIG. 1

The apparatus comprises a supply container 1 for the test strips 13. The supply container 1 is provided with an orifice 14 which, in practice, is closed by means of the transport device 12. A bar 11 projects into the orifice 14 and is arranged moveably on the supply container or the like. According to FIG. 1, the transport device 12 comprises a cylindrical roller 2, on the outer surface of which are arranged drivers 3. The drivers 3 each pick up a test strip 13 from the supply container. To guarantee that the test strips will slip down and to prevent them from forming bridges, a bar 11 is arranged in the orifice and is moved up and down by means of noses 10. The drivers 3 transfer the test strips onto a guide plate 7, via which they travel to a following device, for example into a guide 8. If claw-shaped drivers are used, it may be expedient to provide a pawl 6, in order to eject the test strips from the driver so that they do not jam between the driver 3 and the guide plate 7.

The pawl 6 is driven by bolts 4 which are arranged on one end face of the roller. It may be expedient to provide pawls and bolts on both end faces. The bolts 4 take up the pawl, fastened independently of the roller, for example to the bearing block 16, at the tongue 5. The return spring 9 brings the pawl into its initial position as soon as it is released by the bolt 4.

According to FIG. 2, the transport device 12 comprises a conveyor belt 15 which is equipped with drivers 3. The conveyor belt is guided via deflecting rollers 17, 18. The deflecting roller 17 located opposite the orifice 14 in the supply container 1 is equipped with noses 19 which drive the bar 11. The test strips 13 are transferred from the conveyor belt to the guide plate 7 and from there into the guide 8. The edge 20 serves as a stripper for excess test strips 13. 21 denotes a bearing block. The transport device 12 can be driven electrically or in another way.

I claim:
1. An apparatus for separating test strips, comprising:
 a supply container for receiving a plurality of test strips randomly disposed therein, said supply container having an exit orifice;
 a transport device, closely associated with said exit orifice, for separately transferring said test strips from said exit orifice to a guide chute, said transport device including a rotatably mounted roller plate and at least one hook-shaped driver extending from the periphery thereof, said hook-shaped driver defining a slot for receiving one of said test strips therein and for carrying said test strip from said exit orifice to said guide chute;
 a pivotable bar, having a free end extending into said exit orifice, for selectively feeding said test strips into said exit orifice and for preventing blocking of said exit orifice;
 said at least one hook-shaped driver of said roller plate having a nose portion configured to engage said bar as said roller plate is rotated to pivotably move said free end of said bar;
 pawl means, pivotably mounted adjacent to said roller plate, for moving said test strip received in said slot of said driver toward said guide chute, and at least one bolt-like projection, extending from said roller plate, for pivoting said pawl means as said roller plate is rotated; and
 return means, operably connected to said pawl means, for biasing said pawl means toward an initial position.

* * * * *